United States Patent [19]

Ábrahám et al.

[11] Patent Number: 5,801,808
[45] Date of Patent: Sep. 1, 1998

[54] METHOD AND APPARATUS FOR DETERMINING SPECTRAL SENSITIVITY PARAMETERS OF COLOR-SENSITIVITE RECEPTORS IN THE EYE

[76] Inventors: György Ábrahám, Pipiske u. 1-5, fsz. 28, H-1121 Budapest; Gottfriedné Wenzel, Sashegyi út 14, H-1124 Budapest, both of Hungary

[21] Appl. No.: 727,645
[22] PCT Filed: Apr. 14, 1995
[86] PCT No.: PCT/HU95/00009
§ 371 Date: Oct. 15, 1996
§ 102(e) Date: Oct. 15, 1996
[87] PCT Pub. No.: WO95/28125
PCT Pub. Date: Oct. 26, 1995

[30] Foreign Application Priority Data

Apr. 15, 1994 [HU] Hungary ............... P9401083

[51] Int. Cl.$^6$ ............... A61B 3/10; A61B 3/00
[52] U.S. Cl. ............... 351/221; 351/246
[58] Field of Search ............... 351/246, 247, 351/221, 211, 212, 205, 200

[56] References Cited

FOREIGN PATENT DOCUMENTS 0 493 660   7/1992  European Pat. Off. .
233 300     2/1986  Germany .
39 40 158   6/1991  Germany .

*Primary Examiner*—Hung X. Dang
*Attorney, Agent, or Firm*—Young & Thompson

[57] ABSTRACT

Method for determining spectral sensitivity parameters of color-sensitive receptors in the eye, in the course of which at least one testing light beam is introduced onto an area of the retina of an eye to be tested, and at least one sensitivity parameter is determined by detecting a light beam reflected from the retina or by using color perception of the person tested. In addition to said at least one testing light beam, at least one auxiliary light beam of a wavelength falling outside the spectral sensitivity wavelength range of color-sensitive receptor or receptors to be measured is also introduced onto at least the same area of the retina, said at least one auxiliary light beam reducing the sensitivity of color-sensitive receptor or receptors not to be measured. The invention also relates to an apparatus comprising optical means (7, 8, 13, 6) for generating at least one testing light beam and introducing it into the eye to be tested, means (1, 2, 3) for generating at least one auxiliary light beam, said at least one auxiliary light beam reducing the sensitivity of receptor or receptors not to be measured, and means (4, 6, 48) for introducing said at least one auxiliary light beam into the eye to be tested.

20 Claims, 4 Drawing Sheets

METHOD AND APPARATUS FOR DETERMINING SPECTRAL SENSITIVITY PARAMETERS OF COLOR-SENSITIVITE RECEPTORS IN THE EYE

TECHNICAL FIELD

The invention relates to a method and an apparatus for determining spectral sensitivity parameters of colour-sensitive receptors in the eye.

BACKGROUND ART

The human eye is able to detect electromagnetic radiation in the wavelength range of visible light, which extends from approx. 380 nm to 780 nm. The light efficiency of human vision as a function of wavelength is defined by the so-called visibility curve. In the human eye there are three colour-sensitive receptors (pigments) assuring colour vision, called protos which is sensitive to red, deuteros which is sensitive to green, and tritos which is sensitive to violet. Sensation of the yellow colour is aroused by simultaneous stimuli of the protos and the deuteros. Simultaneous stimuli of the tritos and the deuteros causes the vision of the colour turquoise, while simultaneous stimuli of the tritos and the protos leads to the sensation of the colour purple. Other transitional shades of colours are produced by simultaneous stimuli of the three receptors with different intensities.

Diagrams of spectral sensitivity of the protos, the deuteros and the tritos for people having normal (average) colour vision are well known (FIG. 1). It is known furthermore that the sensitivity of colour-sensitive receptors grows substantially if the intensity of lighting decreases and it drops significantly if the lighting intensity is higher. This kind of phenomenon is called adaptation, which takes place in each receptor independently of each other to a different extent, if the intensity of lighting does not change in the total spectrum range, but has a lower influence on certain receptors and higher influence on others. This is called chromatic adaptation (Leo M. Hurvich: Color Vision, Sinauer Associates Inc., Sunderland, Mass., USA, 1981, pp. 196–200).

It is well known that people do not have exactly the same colour vision. According to the current state of medical art, there are so-called colour blind people who only see two basic colours instead of three. If there is a lack of protos receptors, the colour blind person is called protanop, in lack of deuteros receptors, we speak about a deuteranop person, and if tritos receptors are missing, the person is called tritanop. Additionally, there are people with anomalous colour vision suffering in parachromatism. Although they have all the three receptors, they have a sensation of colours which deviates from that of a normal person. The most frequent form of anomalous colour vision appears as red-green parachromatism. People suffering in red-green parachromatism do not recognize pseudo-isochromatic tables (known in practice as dotted figures) and they are not able to distinguish between red, yellow and green signals used in traffic control. Different types of parachromatism are described on pages 222–269 of the textbook of Leo M. Hurvich mentioned above.

Since people suffering in parachromatism are handicapped in numerous walks of life vis-a-vis individuals of normal colour vision, various approaches have already been recommended for correcting the error of colour vision. In the international application No. PCT/HU93/00045 filed on 18 Aug. 1993, the difference between an eye with colour vision to be corrected and the eye with normal colour vision is compensated by a colour filter of a transmission characteristic appropriately selected on the basis of the abnormal spectral sensitivity of the protos, deuteros and tritos receptors of the eye with a colour vision to be corrected. Consequently, to select the colour filter, the spectral sensitivity curves of the person suffering in parachromatism must be measured and the displacement of the curves along the wavelength must be determined.

It is known that the spectral sensitivities of receptors in the eye can be determined by individual measurements (W. B. Marks, W. H. Dobbelle, E. F. Mac Nichol: Visual Pigments of Single Primate Cones, Science, Vol. 143, March 1964). Rushton performed microspectrographic measurements on eyes of living human beings and monkeys (W. A. H. Rushton: Visual Pigments and Color Blindness, Scientific American, March 1975). In this method, a thin monochromatic light beam is imaged on the retina through the pupil of the eye to be tested, with the size of the light beam—when reaching the retina—not exceeding that of a cone bearing a protos, deuteros or tritos receptor. The intensity of the light beam is continuously measured prior to entering and also after being reflected by the receptor. The difference of the two corresponds to the intensity of light absorbed by the given receptor, which is characteristic of the receptor's sensitivity in the given wavelength. By altering the wavelength of the testing light beam, the spectral sensitivity curve of the given receptor can be determined. Since the sensitivity of one receptor on one cone is measured at a time, in this method it is not a problem that the spectral sensitivity ranges of the receptors are in overlap in most part of the visible spectrum. However, the measurement of the extremely low light intensity and the implementation of demanding measuring conditions do cause a problem.

A test similar to the one described above has been carried out by a spectrophotometric measurement on colour blind people or on samples removed from the person's retina (L. C. Thomson, W. D. Wright: The Convergence of the Tritanopic Confusion Loci and the Derivation of the Fundamental Response Functions, JOSA, 1953, Vol. 43, No. 10, pp. 890–894). These persons have one or more receptors missing, therefore the overlap of spectral sensitivity ranges does not confuse the measurement and so it is not necessary to aim the measurement at a single cone having one type of receptor. However, this method is only suitable for testing colour blind people and not for examining people suffering in parachromatism or having normal colour vision.

According to another method, the spectral sensitivity curves of receptors can be defined by a mathematical method from results of colour mixing measurements (K. Wenzel and G. Szasz: Numerical method for determining simultaneous functions having been measured with an indirect measuring method (in Hungarian), Finommechanika-Mikrotechnika, 1985, Vol. 24, No. 8/9, pp. 250–252). Results obtained by this computing method are in agreement with the results of said microspectrographic measurements, however, the measurements and the calculations are time-consuming.

These known methods, however, are relatively complicated and require costly equipment as well as operating personnel of special qualifications. Exactly because of the above mentioned method for improving parachromatism, a measuring method and an apparatus enabling determination of the spectral sensitivity of each receptor of individuals in a wide circle would be of high significance.

DISCLOSURE OF INVENTION

The object of the present invention is to establish a method by which the spectral sensitivity parameters of colour-sensitive receptors in the eye can be determined in a simple and relatively rapid way. It has also been an objective to provide an apparatus which can be applied in general ophthalmologic practice for determining the spectral sensitivity parameters of colour-sensitive receptors in the eye.

Consequently, on the one hand the invention is a method for determining spectral sensitivity parameters of colour-sensitive receptors in the eye, in the course of which at least one testing light beam is introduced onto an area of the retina of an eye to be tested, and at least one sensitivity parameter is determined by detecting a light beam reflected from the retina or by using colour perception of the person tested. The method is caracterized in that, in addition to said at least one testing light beam, at least one auxiliary light beam of a wavelength falling outside the spectral sensitivity wavelength range of colour-sensitive receptor or receptors to be measured is also introduced onto at least the same area of the retina, said at least one auxiliary light beam reducing the sensitivity of colour-sensitive receptor or receptors not to be measured.

According to the invention, in order to determine the spectral sensitivity of colour-sensitive receptors of the selected type, the two other types of colour-sensitive receptors can be eliminated from the measurement. This is carried out in a way that these receptors are "blinded" with at least one auxiliary light beam of appropriately selected intensity and wavelength during the measurement, that is the sensitivity of these receptors is reduced. For example, in order to measure the spectral sensitivity of the protos, by means of an auxiliary light beam the sensitivity of the deuteros and the tritos is reduced so much that the response to the testing light beam is practically fully given by the protos. If the spectral sensitivity of the deuteros is to be measured, it is of preference to apply two auxiliary light beams, one of them reducing the sensitivity of the tritos and the other reducing the sensitivity of the protos.

According to the invention it is also possible to use a single auxiliary light beam of a wavelength falling outside the spectral sensitivity wavelength range of two colour-sensitive receptors, e.g. protos and deuteros to be measured jointly, and falling into the spectral sensitivity of the third colour-sensitive receptor, e.g. tritos, thereby reducing its sensitivity.

According to a preferred embodiment, said at least one testing light beam comprises a first testing light beam and a second testing light beam, said first testing light beam being of variable intensity and having a wavelength falling into the sensitivity wavelength range of the colour-sensitive receptor or receptors to be measured is introduced onto one zone of the retina, said second testing light beam being of variable wavelength and of constant intensity is introduced onto another zone of the retina, the wavelength of the said second testing light beam is varied step-by-step, and an identical visual perception in two fields of vision corresponding said zones for the person tested is set by adjusting the intensity of said first testing light beam at each wavelength value of said second testing light beam. By this method, the spectral sensitivity curve of the colour-sensitive receptor to be measured can be plotted.

In such a wavelength range where two receptors are sensitive, one can determine a wavelength value where only one of the receptors is sensitive, i.e. the sensitivity limit of the other receptor. According to the method above, this is the wavelength value at which setting an identical visual perception is no longer possible.

According to another embodiment of the invention, a single testing light beam of variable wavelength falling into the sensitivity wavelength range of the colour-sensitive receptor to be measured and of constant intensity is introduced onto the retina, and by varying the wavelength of the testing light beam a visual perception of maximum intensity in the field of vision is set for the person tested. In this way, the wavelength value associated with the maximum sensitivity of the given receptor can be identified.

It is also possible that a single testing light beam of variable wavelength falling into the sensitivity wavelength range of the colour-sensitive receptor to be measured and of constant intensity is introduced onto the retina, and by varying the wavelength of the testing light beam two wavelength values are determined between which the tested person sees the image of the testing light beam in the field of vision. The two wavelength values so obtained are the sensitivity limits of the given receptor.

In another embodiment of the method, the sensitivity of one of the colour-sensitive receptors is reduced by applying one auxiliary light beam, a single testing light beam of variable wavelength and of constant intensity is introduced onto the retina, and by varying the wavelength of the testing light beam a wavelength value is determined at which the tested person perceives a colour change in the field of vision.

In a further embodiment of the method according to the invention, a single testing light beam is introduced onto the retina, the spectral intensity of the testing light beam introduced and that of a light beam reflected from the retina are measured, and the spectral sensitivity curve of the colour-sensitive receptor to be measured is determined on the basis of said two spectral intensities. By this approach, again the spectral sensitivity curve of the receptor to be measured is obtained. Preferably, the spectral intensity of the testing light beam and that of the reflected light beam are measured alternately in time by a monochromator and an associated line detector, so the measurement errors are mostly eliminated.

The measurement can be carried out advantageously in a way that a difference between spectral intensities of the testing light beam and the reflected light beam is determined and said difference is corrected by a spectral correctional function corresponding to tissues of the retina other than the colour-sensitive receptors and optical elements in the path of the testing and reflected light beams. The spectral correctional function can be determined by introducing a single testing light beam and two auxiliary light beams reducing the sensitivity of all the three colour-sensitive receptors, measuring the spectral intensity of the testing light beam introduced and that of the light beam reflected from the retina, and establishing the difference between the measured spectral intensities. It is also possible to determine the spectral correctional function by reflection measurement carried out on a normal eye without the application of any auxiliary light beam. The spectral sensitivity obtained by this measurement deviates exactly by the spectral correctional function from the known spectral sensitivity of the normal eye (visibility curve).

Preferably, the method according to the invention may be carried out so that said at least one auxiliary light beam and said at least one testing light beam are introduced onto the retina continuously and simultaneously. It is advantageous that said at least one testing light beam is introduced on a retina area of not greater than 2° and said at least one auxiliary light beam is introduced on a retina area of at least 5°. If the at least one testing light beam is introduced on a retina area of approximately 2°, it is of preference to introduce the at least one auxiliary light beam on a retina area of about 10°.

On the other hand, the invention is an apparatus for determining spectral sensitivity parameters of colour-sensitive receptors in the eye, which comprises optical means for generating at least one testing light beam and introducing it into the eye to be tested. The apparatus is characterized by, in addition to said optical means, comprising means for generating at least one auxiliary light beam of a wavelength falling outside the spectral sensitivity wavelength range of colour-sensitive receptor or receptors to be measured, said at least one auxiliary light beam reducing the sensitivity of receptor or receptors not to be measured, and means for introducing said at least one auxiliary light beam into the eye to be tested.

In a preferred embodiment of the apparatus, said optical means include means for generating a first testing light beam of variable wavelength and of constant intensity, means for generating a second testing light beam of constant or variable wavelength and of variable intensity, said means for generating a second testing light beam are provided with an intensity meter, and means for introducing said first and second testing light beams onto two zones of the retina of the eye to be tested.

In another embodiment of the apparatus, said optical means include means for generating a single testing light beam of variable wavelength and of constant intensity and means for introducing said single testing light beam onto the retina of the eye to be tested.

A third embodiment of the apparatus is characterized in that said optical means include means for generating a single testing light beam with a spectrum covering the wavelength range of visible light, and means for introducing said single testing light beam onto the retina of the eye to be tested, and that the apparatus further comprises means for measuring spectral intensity of said single testing light beam and that of a light beam reflected from the retina of the eye to be tested. This embodiment preferably comprises means for applying said single testing light beam and the light beam reflected from the retina of the eye alternately in time to light input of said means for measuring spectral intensity.

Based on the apparatus according to the invention, a measuring instrument can be built, which can be used in wide circles in ophthalmologic practice for recording spectral sensitivity parameters of colour-sensitive receptors of people suffering in parachromatism, which data are necessary for making glasses or contact lenses for improving parachromatism.

BRIEF DESCRIPTION OF THE DRAWINGS

Hereinafter, the invention will be described by means of preferred embodiments as shown in the drawings, where.

MODES FOR CARRYING OUT THE INVENTION

In the figures identical elements or elements of identical functions are marked by the same reference signs.

Figure 1:
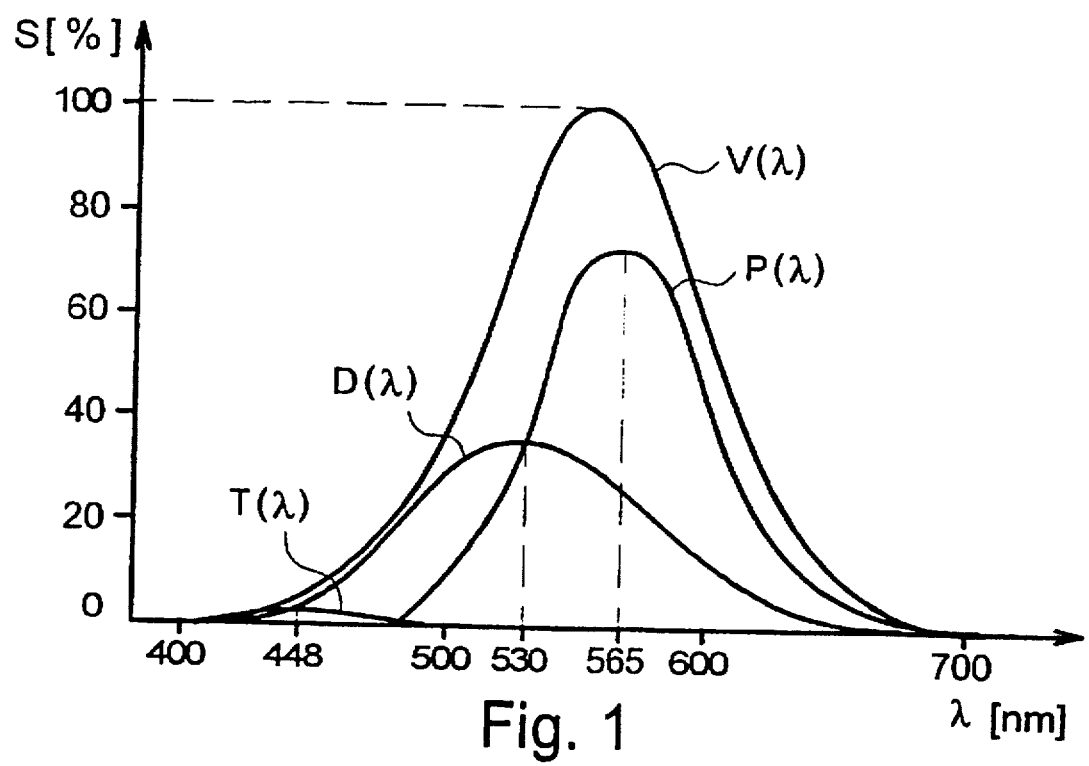
FIG. 1 is a diagram depicting visibility curve of a normal human eye and spectral sensitivity curves of colour-sensitive receptors thereof.

FIG. 1 depicts a visibility curve $V(\lambda)$ showing spectral light efficiency of a normal human eye, and spectral $P(\lambda)$, $D(\lambda)$ and $T(\lambda)$ sensitivity curves of colour-sensitive receptors in a normal human eye, where on the vertical axis the relative spectral sensitivity S in % and on the horizontal axis the wavelength $\lambda$ in nm are shown. The visibility curve $V(\lambda)$ is a resultant of the sensitivity curves $P(\lambda)$, $D(\lambda)$ and $T(\lambda)$. It can be seen that sensitivity curve $P(\lambda)$ of the protos has a maximum at approx. 565 nm, the sensitivity curve $D(\lambda)$ of the deuteros has a maximum at approx. 530 nm and the sensitivity curve $T(\lambda)$ of the tritos has a maximum at approx. 448 nm.

Figure 2:
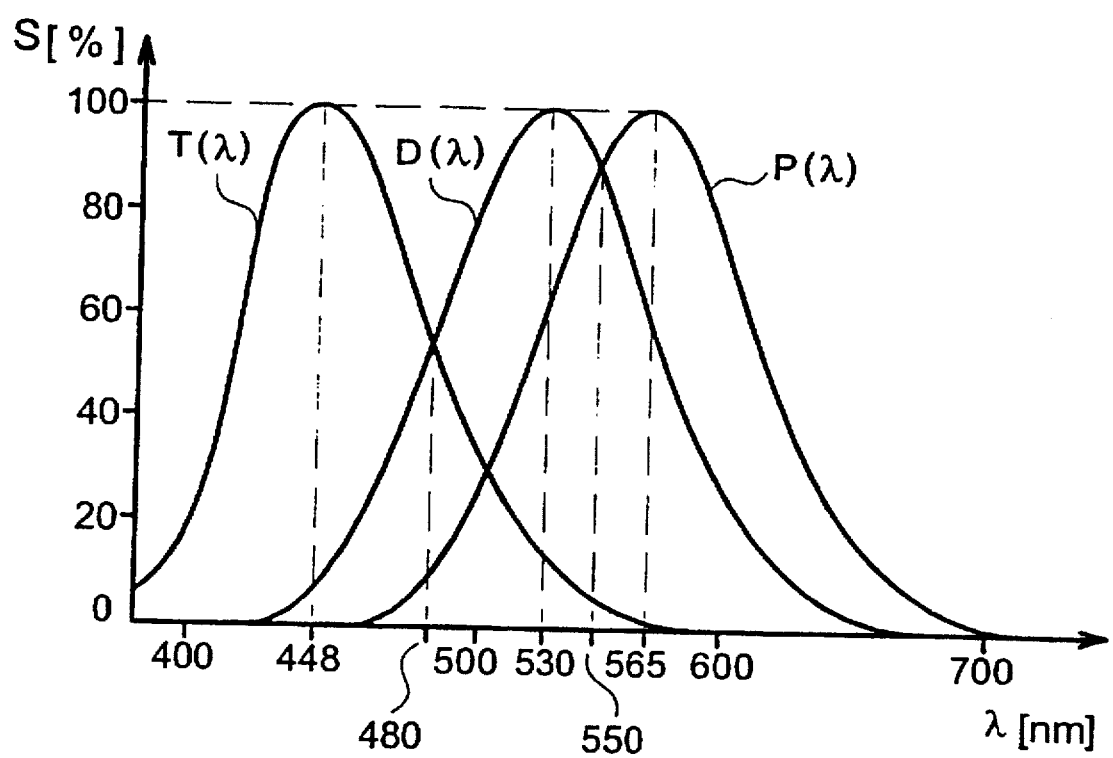
FIG. 2 is a diagram depicting normalized spectral sensitivity curves of colour-sensitive receptors of a normal human eye.

In FIG. 2 normalized spectral sensitivity curves $P(\lambda)$, $D(\lambda)$ and $T(\lambda)$ of colour-sensitive receptors in a normal human eye are shown, where on the vertical axis the relative spectral sensitivity S in % and on the horizontal axis the wavelength $\lambda$ in nm is depicted. The intersection point of the normalized sensitivity curve $T(\lambda)$ and $D(\lambda)$ is approx. at 480 nm and that of the normalized sensitivity curves $D(\lambda)$ and $P(\lambda)$ is approx. at 550 nm. The maximum and intersection points and to a certain extent the shapes of the sensitivity curves may be different for each group of people.

Figure 3:
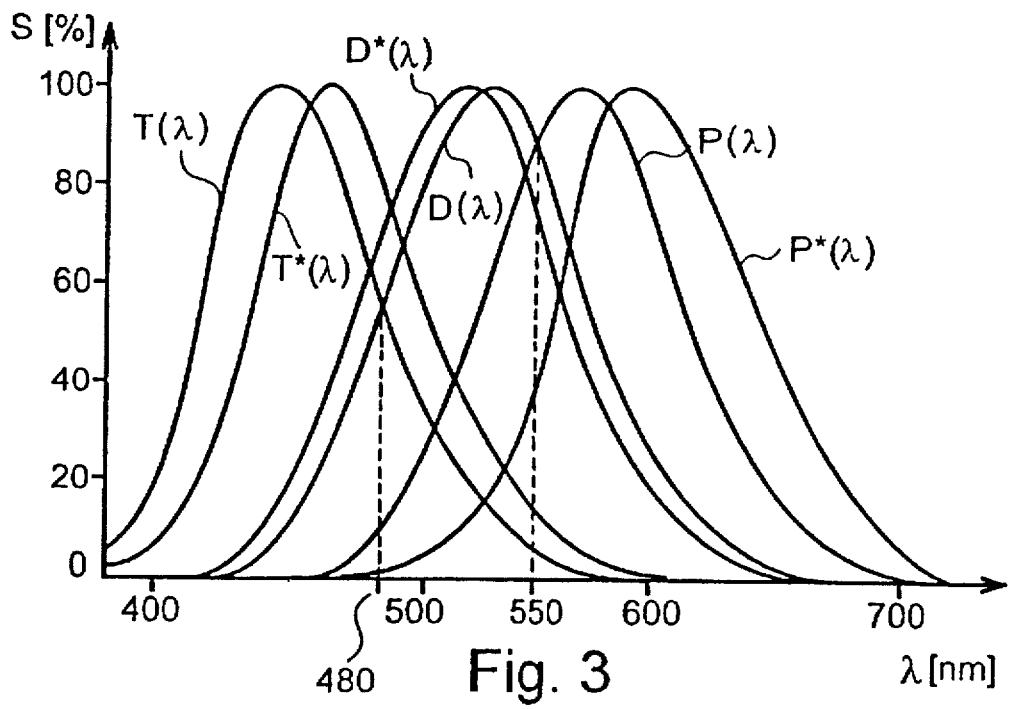
FIG. 3 is a diagram showing spectral sensitivity curves of colour-sensitive receptors of a normal human eye and those of a human eye exhibiting colour vision anomaly.

In FIG. 3, the sensitivity curves $P(\lambda)$, $D(\lambda)$ and $T(\lambda)$ of the colour-sensitive receptors in the normal human eye and the sensitivity curves $P^*(\lambda)$, $D^*(\lambda)$ and $T^*(\lambda)$ of the respective receptors of an eye with anomalous colour vision are shown. Sensitivity curve $P^*(\lambda)$ is displaced in the direction of larger wavelengths vis-a-vis the sensitivity curve $P(\lambda)$ and its shape is also different from that of sensitivity curve $P(\lambda)$. Sensitivity curve $D^*(\lambda)$ is shifted in the direction of the shorter wavelengths as against the sensitivity curve of $D(\lambda)$ and its shape is practically identical with that of sensitivity curve $D(\lambda)$. And, sensitivity curve $T^*(\lambda)$ is displaced in the direction of longer wavelengths vis-a-vis the sensitivity curve $T(\lambda)$ and its shape is also different from that of the sensitivity curve $T(\lambda)$. The rates of displacement are in turn: $\Delta\lambda_p=17.5$ nm, $\Delta\lambda_D=-4$ nm, $\Delta\lambda_T=17.5$ nm.

The present invention applies to a measuring method and apparatus by means of which series measurements may be carried out in vivo on a human eye under routine test conditions, in order to determine parameters of the spectral sensitivity curves of the colour-sensitive receptors. The most important parameters of spectral sensitivity curves are the following:

a) wavelength values of maxima of the curves;

b) values of maxima of the curves which characterize an eye without colour adaptation, e.g. an eye adapted to the colour white;

c) threshold sensitivity of the curves;

d) the range of change in curve size, i.e. the colour adaptation range of the receptors;

e) the sensitivity wavelength range of curves, i.e. the wavelength range between the limits of light perception by the given type of receptors;

f) the shape of the curves, which describes the rate of the functions between the maximum point and the limits of the sensitivity wavelength range.

We have recognized that concerning the shape as per point f) the differences are little in the human population, and in most cases it is sufficient to specify differences between individuals by parameters on the basis of points a) and e), and in many cases a person suffering in parachromatism can be sufficiently characterized by one of those parameters, only.

The measurement based on the invention may be carried out in a way that a light beam of known spectral composition is imaged on the retina of the eye to be tested, where it will stimulate the receptor to be measured. One part of the light is absorbed in the receptor and another part is reflected therefrom. The absorbed part can be deemed proportionate to the spectral sensitivity of the receptor.

In order to enable the measurement of the spectral sensitivity curve of one receptor, the other two receptors must be eliminated from the measurement, because the sensitivity curves of the receptors overlap each other. Elimination is carried out by a temporary blinding, preferably on an area of at least 5° of the retina, by at least one auxiliary light beam, the wavelength of which being outside the sensitivity wavelength range of the receptor to be measured and within the sensitivity wavelength ranges of the receptors to be blinded. After eliminating the two other receptors in this way, a testing light beam is introduced onto the same or smaller area of the retina. The testing light beam is applied on an area of not greater than 2° of the retina. In this way, the receptors not to be measured are blinded not only on the area where the measurement is carried out, but in its surroundings, too. The testing light beam is reflected from the retina and the light beam coming back from the eye is measured. The testing light beam entering the eye is also measured. Both measurements are of spectral character, consequently we know the spectral composition of both the ingoing and the reflected light. On the basis of the difference between the two spectra and the correctional function described above, spectral characteristics of the partly blinded retina, that is those of the receptors to be measured, can be determined.

In another embodiment of the invention, instead of measuring the light reflected from the retina, the spectral sensitivity curve of the measured receptors are determined by involving the tested person in the evaluation. In this case the general method applied is that at least one testing light beam is imaged onto the retina of the eye, at least one of them is of variable wavelength, and one or more auxiliary light beams of fixed wavelength is additionally introduced onto the retina. All these light beams are applied simultaneously.

As a result of the auxiliary light beam or light beams of fixed wavelength, the sensitivity of one receptor or two receptors is reduced, i.e. they become insensitive to a certain extent, and then the two other receptors or the third receptor, respectively, are/is stimulated by a testing light of varying wavelength. The visual perception so generated is suitable under certain conditions for determining one or more of the spectral sensitivity function parameters of the receptors tested.

One method of determination is that the tested person alters the wavelength of the testing light beam, while its intensity remains unchanged, until he senses maximum intensity by means of the receptor or receptors to be measured. In this way, the wavelength of the maximum loci of the spectral sensitivity curve of one receptor to be tested, or that of the resultant of spectral sensitivity curves of jointly measured two receptors, can be determined.

According to another method of determination, the tested person adjusts the wavelength rate at which he just detects the given testing light, while changing the wavelength of the testing light beam. In this way the limits of the sensitivity wavelength ranges of one receptor or two receptors to be measured can be determined.

According to a third method, the sensitivity of the protos or tritos is reduced by applying an auxiliary light beam, and the wavelength of a testing light beam is varied until the tested person perceives a colour change in the field of vision. In this way intersection points of sensitivity curves of tritos and deuteros, as well as deuteros and protos, respectively, can be determined. By varying the wavelength in a direction of greater values, blue changes into green at the intersection point of tritos and deuteros, and green changes into red at the intersection point of deuteros and protos.

According to still another method, one or more auxiliary light beams of constant intensity and of constant wavelength are applied in the whole field of vision to reduce the sensitivity of two receptors. The shape of the sensitivity curve of the receptor to be measured can be determined in a way that in addition to the above mentioned auxiliary light beam or light beams, one zone of the field of vision receives a light "A" of variable intensity and of a fixed wavelength falling into the sensitivity wavelength range of the receptor to be measured, and another zone receives a light "B" of a constant intensity and of variable wavelength in an additive way. In this case the tested person is allowed to adjust the intensity of light "A" in order to have a visual perception identical with light "B", the wavelength of which is altered gradually. As a result of the measurement, the intensity of the adjusted light "A" is recorded for each step, and so a function proportional with the sensitivity curve of the measured receptor is obtained.

The next method can be advantageously used in wavelength ranges where two receptors are simultaneously sensitive. By means of the method, a wavelength value can be determined, where only one of the receptors is sensitive and so one limit point of the sensitivity wavelength range of the other of the receptors can be identified. In this method, the person tested observes a divided field of vision. One zone of this field receives light "A" of constant wavelength but of variable intensity, while the other zone receives light "B" of variable wavelength but of constant intensity. The wavelength of light "A" must be selected in a way that it only stimulates one of the receptors. When altering the wavelength of light "B", as long as the receptor corresponding to light "A" are stimulated, the tested person sees the same colour in both zones, but perhaps with different intensities. The deviating intensity will confuse the tested person in determining an accurate colour equality of the two zones. Therefore, we allow the tested person to alter the intensity of light "A" until light "A" also generates the sensation created by light "B". The measurement is carried out in a way that, by altering the wavelength of light "B" in predetermined small steps, it is brought closer to the assumed wavelength value at which the other receptor is also involved. By altering the intensity of light "A", the person examined attempts to create equal colour and intensities. If he succeeds, we alter the wavelength of light "B" further by a small step and then the person tested attempts again to adjust equal colour and intensity. This is repeated until the examined person is no longer able to set the equality of the two zones. He cannot be successful because light "B" now has a wavelength at which the other receptor is also involved, and so the colour sensation generated by the two types of receptors may not be created in the range of light "A", because the latter only affects one of the receptors. The measurement is discontinued at this point and the last wavelength value of light "B" is noted. Thereby the limit point of the sensitivity wavelength range of the other of the receptors has been defined. This method is suitable for example for identifying both limits of the deuteros by applying light "A" selected according to the protos in one case and to the tritos in the other.

Figure 4:
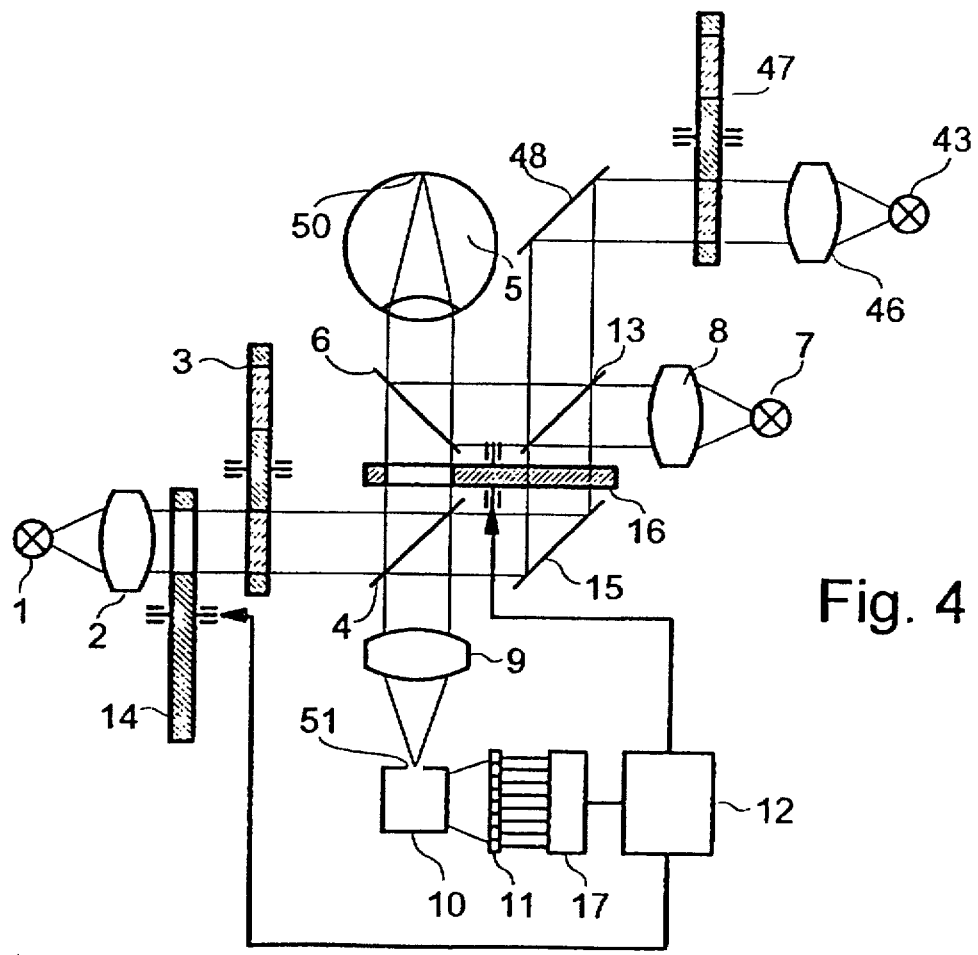
FIG. 4 is a simplified optical sketch of an embodiment of the apparatus according to the invention.

The apparatus according to the invention will be described on the basis of embodiments depicted in the figures. In FIG. 4 three light beams are introduced onto the retina 50 of the eye 5 to be tested. From a light source 1, the light of which can be varied in time, through a condenser lens 2, a mechanical chopper 14 and a variable colour filter 3, a light beam falls onto a semi-transparent mirror 4, where the light beam changes its direction and passes through one of the apertures of a shutter 16 being open or closed in time, then entering the eye 5. This first auxiliary light beam blinds one of the receptors, e.g. the protos, that we do not intend to measure. The colour filter 3 is to be set so that the first auxiliary light beam is of a wavelength which falls outside the spectral sensitivity wavelength range of the receptor, e.g. the deuteros, to be measured. From another light source 43, through a condenser lens 46 and a variable colour filter 47, a second light beam changes its direction at mirrors 48, 13 and 6 and also enters the eye 5. This second auxiliary light beam reduces the sensitivity of another receptor, e.g. the tritos, that we do not intend to measure either. The colour filter 47 is to be set so that the second auxiliary light beam is of a wavelength which falls outside the spectral sensitivity wavelength range of the receptor, e.g. the deuteros, to be measured. From a third light source 7, through a condenser lens 8 and a semi-transparent mirror 13; a third light beam changes its direction at the semi-transparent mirror 6 and also enters the eye 5. This light beam represents a testing light beam for the receptor to be measured, e.g. for the deuteros.

The light beam reflected from the retina 50 of eye 5 exits from the eye 5 and passing through semi-transparent mirror 6 and then through the aperture of the shutter 16 and through semi-transparent mirror 4, it reaches a lens 9. The lens 9 focuses the light beam to input aperture 51 of a monochromator 10 and so the light exiting from the monochromator 10 in the form of a light beam split into colours illuminates a line detector 11. Each element of the line detector 11 senses the light in a short wavelength range, and all the detector elements detect the light spectrum. From the line detector 11 the spectral light intensity information reaches a computer 12 through an interface 17 in the form of electric signals.

In another position, the shutter 16 ensures that no light falls on the lens 9 from the eye 5. In this position the light of light source 7, coming through lens 8, semi-transparent mirror 13, an aperture of shutter 16, mirror 15 and semi-transparent mirror 4, is focused by lens 9 to the inlet aperture 51 of monochromator 10 and so line detector 11 is able to detect the light spectrum of light source 7. Consequently, alternating in time, computer 12 receives electric signals corresponding to light spectrum of the light source 7 and the light beam reflected from the retina 50, respectively. Computer 12 controls the chopper 14 and the shutter 16, and determines the spectral sensitivity of the receptor, e.g. the deuteros, to be measured from signals corresponding to the two spectra.

Figure 5:
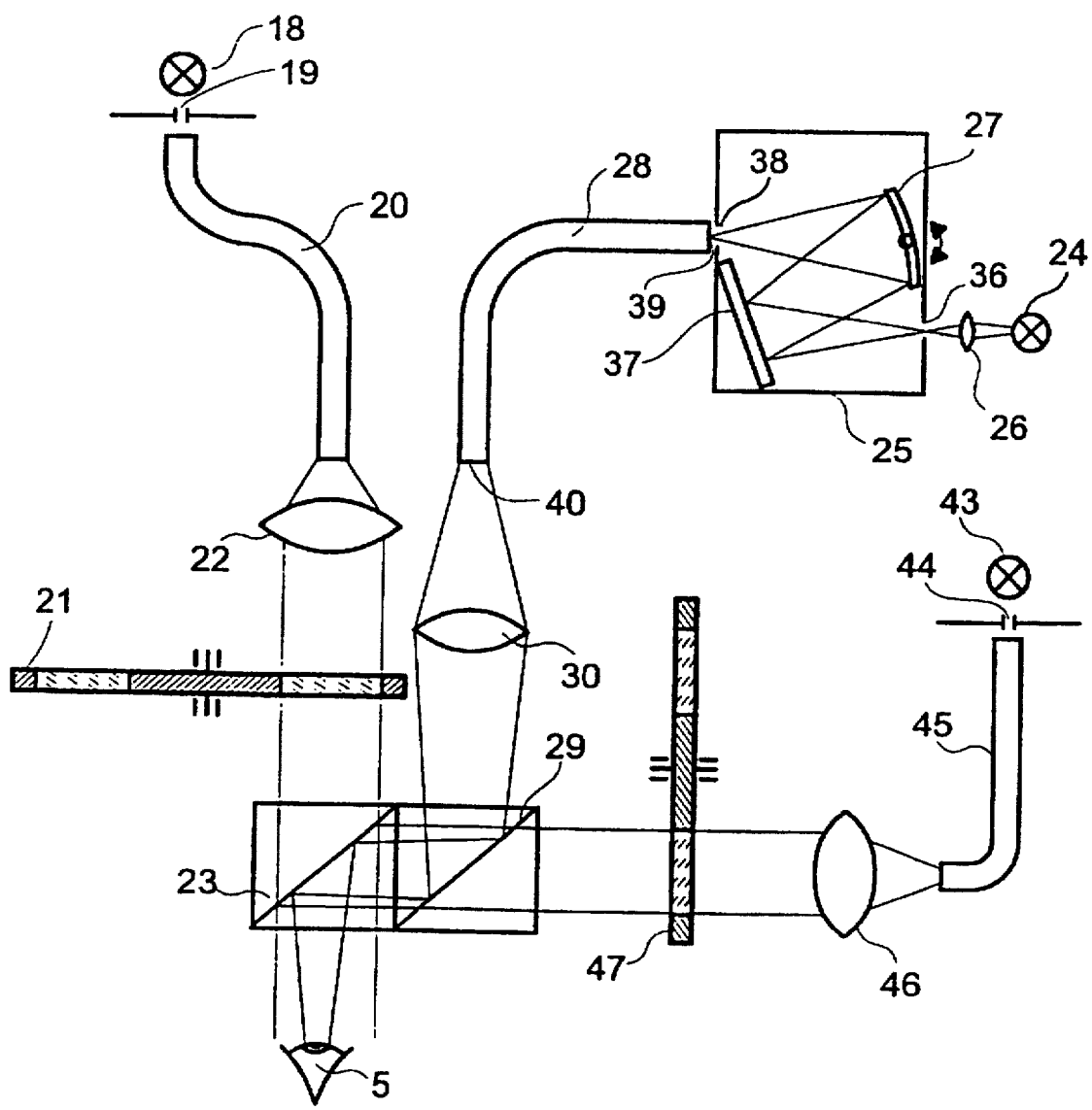
FIG. 5 is a simplified optical sketch of another embodiment of the apparatus according to the invention.

In FIG. 5 three light beams are introduced into eye 5 to be tested. The intensity of the light from a light source 18 can be adjusted to the required value electrically or by means of a variable mechanical diaphragm 19. The light reaches through fibre optics 20 and collective lens 22 a variable colour filter 21 and then passing a semi-transparent prism 23 enters the eye 5. This first auxiliary light beam serves for reducing the sensitivity of one of the receptors which is not to be measured. From another light source 43, through diaphragm 44, fibre optics 45, condenser lens 46, variable colour filter 47, semi-transparent prism 29, a second light beam changes its direction at semi-transparent prism 23 and also enters the eye 5. This second auxiliary light beam reduces the sensitivity of the other receptor not to be measured. The light of a third light source 24 is imaged by lens 26 to inlet aperture 36 of a monochromator 25. The light beam entering through the inlet aperture 36 is reflected by mirror 37 to an optical grid 27, by turning of which one end 39 of fibre optics 28 is illuminated by a light beam of varying wavelength, this end 39 being located at an outlet aperture 38 of the monochromator 25. The other end 40 of fibre optics 28 is viewed by the eye 5 through prisms 23 and 29 and through ocular lens 30. The light beam emitted from the monochromator 25 is a testing light beam. In the eye 5, the three different light beams in space and/or time impose different stimuli on the various receptors of the retina, as a result of which the examined person observes colour and/or intensity conformities, and detects the disappearance/appearance of details in certain zones of the field of vision, respectively.

Figure 6:
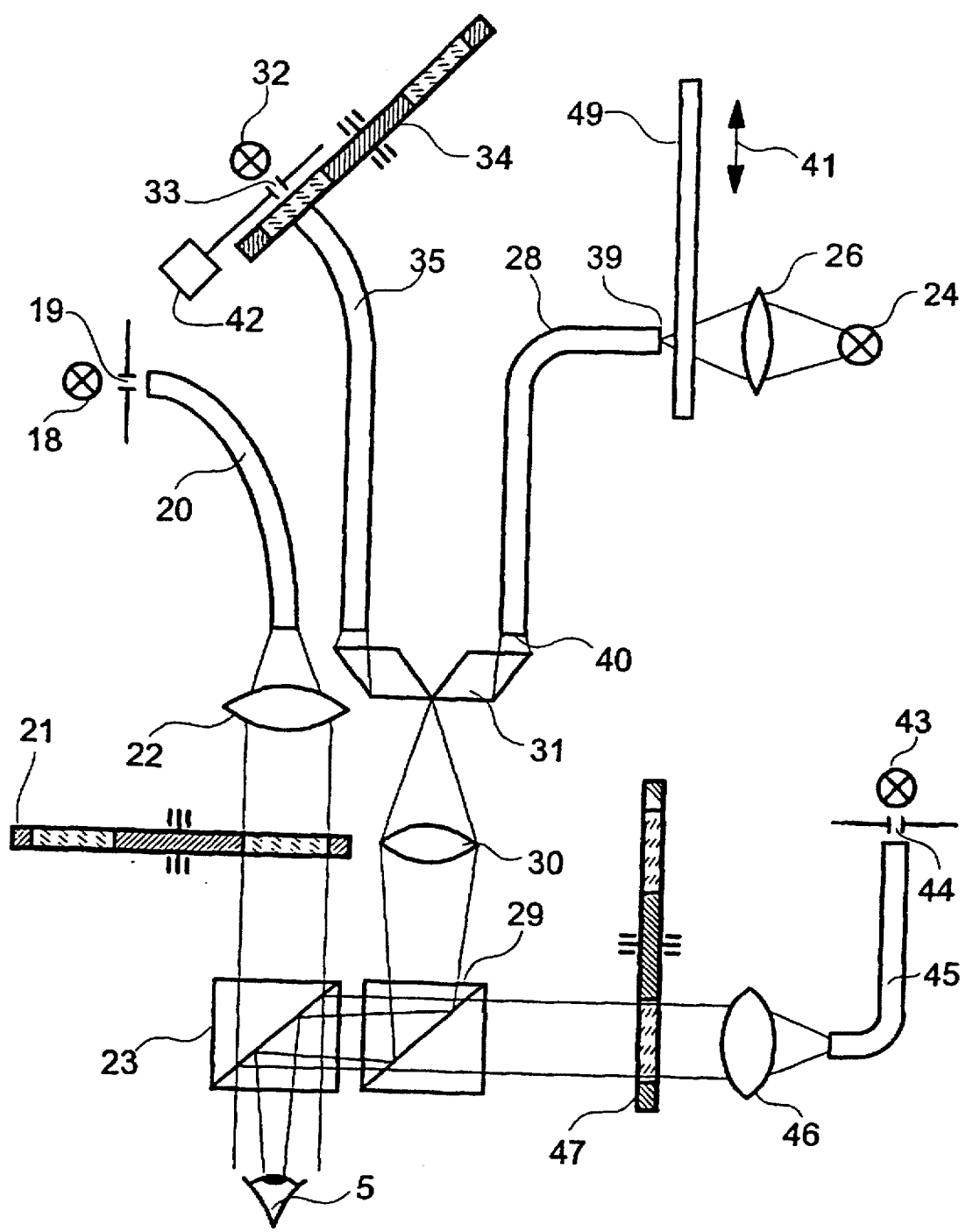
FIG. 6 is a simplified optical sketch of a third embodiment of the apparatus according to the invention.

Another form of implementation of the apparatus according to the invention is shown in FIG. 6, which is similar to the embodiment depicted in FIG. 5. Therefore, elements of FIG. 6 different from those of FIG. 5 will be described, only. The plane of a double prism 31 is seen sharply by the eye 5. The two halves of the double prism 31 receive different testing light beams. The right hand side half receives a first testing light beam of variable wavelength and of constant intensity. This beam is coming from light source 24 through lens 26, continuously variable interference filter 49, which can be adjusted by moving it according arrow 41, and fibre optics 28. The interference filter 49 has the same function as the monochromator 25 in FIG. 5. The left hand side half of the double prism 31 receives a second testing light beam of variable wavelength and of variable intensity from a light source 32 through mechanical diaphragm 33, variable colour filter 34 and fibre optics 35. The intensity can be varied by setting the variable diaphragm 33. The intensity value set by the diaphragm 33 is provided by an intensity meter 42, e.g. by adjusting means having a scale. In conformity with the measuring method used the colour filter 34 can be an interference filter adjustable to some discrete wavelength values or an interference filter continuously adjustable.

The apparatus shown in FIG. 6 is either used so that both light sources 18 and 43 are switched on, thereby providing blinding for two receptors not to be measured, to which the two zones of the field of vision receiving different illumination and generated by the double prism 31 is added, or so that only one of the light sources 18 and 43 is switched on, thereby providing one auxiliary light beam, only for blinding one receptor or in some cases two receptors.

According to a first measurement method by using the apparatus of FIG. 6, the tested person has to set an equal visual perception in two zones of the field of vision of the double prism 31 by altering the intensity of light beam coming from light source 32 by adjusting diaphragm 33, while through gradual moving of the interference filter 49, the wavelength is varied in the right hand side half of the double prism 31. As a direct result of the measurement, the wavelength of the colour adjusted by interference filter 49 and the value of the associated intensity as provided by meter 42, adjusted by the tested person, are registered. From these values the spectral sensitivity curve of the measured receptor can be derived.

In another measurement method the apparatus as shown in FIG. 6 is used to register the positions of interference filter 49 corresponding to wavelength values where the examined person could, or could not set equal colour and intensity in the two zones of the field of vision.

According to a third measurement method, the apparatus of FIG. 6 is used to determine the spectral sensitivity curve of the receptor to be measured. For this method the colour filter 34 should be continuously variable. The sensitivities of the receptors not to be measured are reduced by auxiliary light beams from light sources 18 and 43. It may be that one auxiliary light beam is enough for blinding the two receptors not to be measured, in this case one of the light sources 18 and 43 is switched off. In the right hand side half of the double prism 31 a first testing light beam of variable wavelength and of constant intensity is introduced, and the tested person has to adjust the wavelength by setting the interference filter 49 until a maximum intensity is perceived, at which wavelength the sensitivity of the receptor is the greatest. In the left hand side half of the double prism 31 a second testing light beam of wavelength continuously variable by interference filter 34 is introduced, the intensity of the second testing light beam being adjustable by diaphragm 33. The value of the intensity is provided by meter 42. The wavelength of colour filter 34 is also set for a maximum sensitivity. Then, the tested person sets the intensity by adjusting diaphragm 33 so that the intensities perceived in both halves of the double prism 31 are equal, and the intensity value given by meter 42 is recorded. Then, a smaller intensity value is set by diaphragm 33 and the tested person adjusts the wavelength by varying the interference filter 49 until the same intensity is perceived in both halves of the double prism 31. This occurs at two wavelength values on opposite sides of the maximum wavelength value. Both values are recorded. The steps of decreasing the intensity and adjusting the wavelength are repeated as necessary in order to determine the sensitivity curve of the receptor measured from the related intensity and wavelength values.

It is evident to those skilled in the art that the above disclosures are exemplary only and that various other embodiments of the invention may be made or used within the scope of the present invention as defined by the following claims. E.g. it is possible that for some purpose the apparatus according to the invention has only one device for generating one auxiliary light beam, or the optical elements as shown in the drawings can be replaced by other equivalent optical elements.

We claim:

1. A method for determining spectral sensitivity parameters of color-sensitive receptors in the eye, comprising introducing at least one testing light beam onto an area of the retina of an eye to be tested, introducing at least one auxiliary light beam of a wavelength falling outside the spectral sensitivity wavelength range of at least one color-sensitive receptor to be measured at least onto said area of the retina, said at least one auxiliary light beam reducing the sensitivity of at least one color-sensitive receptor not to be measured, and determining at least one sensitivity parameter by detecting a light beam reflected from the retina or by using color perception of the person tested.

2. The method according to claim 1, wherein said at least one auxiliary light beam comprises one light beam or two light beams, the wavelength of which falling outside the spectral sensitivity wavelength range of one color-sensitive receptor to be measured, said one light beam or two light beams reducing the sensitivity of the two other color-sensitive receptors.

3. The method according to claim 1, wherein said at least one auxiliary light beam comprises a single light beam, the wavelength of which falling outside the spectral sensitivity wavelength range of two color-sensitive receptors to be measured jointly, said single light beam reducing the sensitivity of the third color-sensitive receptor.

4. The method according to claim 1, wherein said at least one testing light beam comprises a first testing light beam and a second testing light beam, and comprising the steps of introducing said first testing light beam being of variable intensity and having a wavelength falling into the sensitivity wavelength range of the at least one color-sensitive receptor to be measured onto one zone of the retina, introducing said second testing light beam being of variable wavelength and of constant intensity onto another zone of the retina, varying the wavelength of the said second testing light beam step-by-step, and setting an identical visual perception in two fields of vision corresponding said zones for the person tested by adjusting the intensity of said first testing light beam at each wavelength value of said second testing light beam.

5. The method according to claim 4, wherein for measuring one color-sensitive receptor, spectral sensitivity curve of said color-sensitive receptor is determined on the basis of wavelength values of said second testing light beam and intensity values of said first testing light beam, said intensity values being necessary for an identical visual perception.

6. The method according, to claim 4, wherein for measuring two color-sensitive receptors, a wavelength value of said second testing light beam is determined at which it is no longer possible to set an identical visual perception.

7. The method according to claim 1, wherein a single testing light beam of variable wavelength falling into the sensitivity wavelength range of the color-sensitive receptor to be measured and of constant intensity is introduced onto the retina, and by varying the wavelength of said single testing light beam a visual perception of maximum intensity in the field of vision is set for the person tested.

8. The method according to claim 1, wherein a single testing light beam of variable wavelength falling into the sensitivity wavelength range of the color-sensitive receptor to be measured and of constant intensity is introduced onto the retina, and by varying the wavelength of said single testing light beam two wavelength values are determined between which the tested person sees the image of the testing light beam in the field of vision.

9. The method according to claim 1, wherein the sensitivity of one of the color-sensitive receptors is reduced by applying one auxiliary light beam, a single testing light beam of variable wavelength and of constant intensity is introduced onto the retina, and by varying the wavelength of said single testing light beam a wavelength value is determined at which the tested person perceives a color change in the field of vision.

10. The method according to claim 1, wherein a single testing light beam is introduced onto the retina, spectral intensity of said single testing light beam introduced and that of a light beam reflected from the retina are measured, and the spectral sensitivity curve of the color-sensitive receptor to be measured is determined on the basis of said two spectral intensities.

11. The method according to claim 10, wherein the spectral intensity of said single testing light beam and that of the reflected light beam are measured alternately in time by a monochromator and an associated line detector.

12. The method according to claim 10, herein a difference between spectral intensities of said single testing light beam and the reflected light beam is determined and said difference is corrected by a spectral correctional function corresponding to tissues of the retina other than the color-sensitive receptors and optical elements in the path of the testing and reflected light beams.

13. The method according to claim 12, wherein said spectral correctional function is determined by introducing a single testing light beam and two auxiliary light beams reducing the sensitivity of all the three color-sensitive receptors, measuring the spectral intensity of the testing light beam introduced and that of the light beam reflected from the retina, and establishing the difference between the measured spectral intensities.

14. The method according to claim 1, wherein said at least one auxiliary light beam and said at least one testing light beam are introduced onto the retina continuously and simultaneously.

15. The method according to claim 1, wherein said at least one testing light beam is introduced on a retina area of not greater than 2° and said at least one auxiliary light beam is introduced on a retina area of at least 5°.

16. An apparatus for determining spectral sensitivity parameters of color-sensitive receptors in the eye, comprising optical means for generating at least one testing light beam and introducing it into the eye to be tested, means for generating at least one auxiliary light beam of, a wavelength falling outside the spectral sensitivity wavelength range of at least one color-sensitive receptor to be measured, said at least one auxiliary light beam reducing the sensitivity of at least one color-sensitive receptor not to be measured, and means for introducing said at least one auxiliary light beam into the eye to be tested.

17. The apparatus according to claim 16, wherein said optical means include means for generating a first testing light beam of variable wavelength and of constant intensity, means for generating a second testing light beam of constant or variable wavelength and of variable intensity, said means for generating a second testing light beam being provided with an intensity meter, and means for introducing said first and second testing light beams onto two zones of the retina of the eye to be tested.

18. The apparatus according to claim 16, wherein said optical means include means for generating a single testing light beam of variable wavelength and of constant intensity and means for introducing said single testing light beam onto the retina of the eye to be tested.

19. The apparatus according to the claim 16, wherein said optical means, include means for generating a single testing light beam with a spectrum covering the wavelength range of visible light, and means for introducing said single testing light beam onto the retina of the eye to be tested, and that the apparatus further comprises means for measuring spectral intensity of said single testing light beam and that of a light beam reflected from the retina of the eye to be tested.

20. The apparatus according to claim 19, further comprising means for applying said single testing light beam and the light-beam reflected from the retina of the eye alternately in time to a light input of said means for measuring spectral intensity.

* * * * *